US009486357B2

(12) United States Patent
Peyman

(10) Patent No.: US 9,486,357 B2
(45) Date of Patent: Nov. 8, 2016

(54) OPHTHALMIC DRUG DELIVERY SYSTEM AND METHOD

(76) Inventor: Gholam A. Peyman, Sun City, AZ (US)

(*) Notice: Subject to any disclaimer, the term of this patent is extended or adjusted under 35 U.S.C. 154(b) by 717 days.

(21) Appl. No.: 13/457,568

(22) Filed: Apr. 27, 2012

(65) Prior Publication Data

US 2012/0213841 A1 Aug. 23, 2012

Related U.S. Application Data

(60) Division of application No. 12/985,758, filed on Jan. 6, 2011, now abandoned, which is a continuation-in-part of application No. 12/611,682, filed on Nov. 3, 2009, now abandoned.

(60) Provisional application No. 61/114,143, filed on Nov. 13, 2008.

(51) Int. Cl.
*A61F 9/00* (2006.01)
*A61K 9/00* (2006.01)
*A61K 31/365* (2006.01)
*A61K 31/436* (2006.01)
*A61K 38/13* (2006.01)

(52) U.S. Cl.
CPC ............ *A61F 9/0017* (2013.01); *A61K 9/0051* (2013.01); *A61K 31/365* (2013.01); *A61K 31/436* (2013.01); *A61K 38/13* (2013.01)

(58) Field of Classification Search
CPC A61F 9/0017; A61K 9/0051; A61K 31/365; A61K 31/436; A61K 38/13
See application file for complete search history.

(56) References Cited

U.S. PATENT DOCUMENTS

| 3,096,076 | A | * | 7/1963 | Walli | 254/89 H |
| 4,781,675 | A | | 11/1988 | White | |
| 5,178,604 | A | | 1/1993 | Baerveldt et al. | |
| 5,366,501 | A | | 11/1994 | Langerman | 623/6.42 |
| 5,370,607 | A | | 12/1994 | Memmen | |
| 5,454,796 | A | | 10/1995 | Krupin | |
| 5,578,042 | A | * | 11/1996 | Cumming | 606/107 |
| 5,628,795 | A | | 5/1997 | Langerman | 623/4.1 |
| 5,725,493 | A | | 3/1998 | Avery et al. | |
| 5,830,173 | A | | 11/1998 | Avery et al. | |
| 6,117,675 | A | * | 9/2000 | van der Kooy et al. | 435/354 |
| 6,324,429 | B1 | * | 11/2001 | Shire et al. | 607/54 |
| 6,378,526 | B1 | * | 4/2002 | Bowman et al. | 128/898 |
| 6,649,625 | B2 | * | 11/2003 | Azuma et al. | 514/303 |
| 7,090,888 | B2 | | 8/2006 | Snyder et al. | |
| 7,276,050 | B2 | | 10/2007 | Franklin | |
| 7,278,990 | B2 | | 10/2007 | Gwon | 606/5 |
| 7,794,437 | B2 | | 9/2010 | Humayun et al. | |
| 7,824,704 | B2 | | 11/2010 | Anderson et al. | |
| 2002/0071855 | A1 | | 6/2002 | Sadozai et al. | 424/426 |
| 2003/0149479 | A1 | | 8/2003 | Snyder et al. | 623/6.16 |
| 2004/0132725 | A1 | * | 7/2004 | Levitzki et al. | 514/224.5 |
| 2004/0137059 | A1 | * | 7/2004 | Nivaggioli et al. | 424/468 |
| 2005/0064010 | A1 | * | 3/2005 | Cooper et al. | 424/423 |
| 2005/0251236 | A1 | * | 11/2005 | Jeannin et al. | 607/107 |
| 2006/0008506 | A1 | * | 1/2006 | Cipriano De Sousa et al. | 424/427 |
| 2006/0106455 | A1 | * | 5/2006 | Furst et al. | 623/1.31 |
| 2007/0020336 | A1 | * | 1/2007 | Loftsson et al. | 424/486 |
| 2007/0031472 | A1 | * | 2/2007 | Huang et al. | 424/427 |
| 2007/0093892 | A1 | * | 4/2007 | Mackool | 623/6.42 |
| 2008/0027304 | A1 | * | 1/2008 | Pardo et al. | 600/399 |
| 2008/0033351 | A1 | * | 2/2008 | Trogden et al. | 604/57 |
| 2009/0269356 | A1 | * | 10/2009 | Epstein et al. | 424/158.1 |
| 2009/0325959 | A1 | * | 12/2009 | Vittitow et al. | 514/236.5 |
| 2010/0119519 | A1 | | 5/2010 | Peyman | 424/141.1 |

FOREIGN PATENT DOCUMENTS

DE 4424753 * 1/1996 ............ A61F 2/14

OTHER PUBLICATIONS

Alfons Macaya, et al, Cell Death and Associated c-jun Induction in Perinatal Hypoxia-Ischemia. Effect of the Neuroprotective Drug Dexamethasone, 56 Mol. Brain Res. 29 (1998).*
Jayakrishna Ambati, et al, Age-Related Macular Degeneration: Etiology, Pathogenesis, and Therapeutic Strategies, 48 Surv. Ophthalmol. 257 (2003).*
DE4424753 Machine Translation.*
U.S. Appl. No. 12/985,785, filed Jan. 6, 2011.
U.S. Appl. No. 12/611,682, filed Nov. 3, 2009.
U.S. Appl. No. 61/114,143, filed Nov. 13, 2008.
Yi Luo, et al, Cross-linked Hyaluronic Acid Hydrogel Films: New Biomaterials for Drug Delivery, 69 J Control. Rel. 169 (2000).
Peyman, G., et al. Intravitreal injection of therapeutic agents, *Retina*. Jul.-Aug. 2009;29(7):875-912.
Peyman, G., et al. Intravitreal injection of liposome-encapsulated ganciclovir in a rabbit model. *Retina*. 1987;7(4):227-9.
Khoobehi, B., et al. Clearance of sodium fluorescein incorporated into microspheres from the vitreous after intravitreal injection. *Ophthalmic Surg*. Mar. 1991;22(3):175-80.
Berger, et al. Intravitreal Sustained Release Corticosteroid-5-Fluoruracil Conjugate in the Treatment of Experimental Proliferative Vitreoretinopathy. *Investigative Ophthalmology & Visual Science*, Oct. 1996, vol. 37, No. 2, pp. 2318-2325.
Mello-Filho, P., et al. Helical intravitreal triamcinolone acetonide implant: a 6-month surgical feasibility study in rabbits. *Ophthalmic Surg Lasers Imaging*. Mar.-Apr. 2009;40(2):160-8.
Casey, D., et al. Analysis of responses to the Rho-kinase inhibitor Y-27632 in the pulmonary and systemic vascular bed of the rat. *Am J Physiol Heart Circ Physiol*. Jul. 2010;299(1):H184-92.

(Continued)

*Primary Examiner* — Sean Basquill
(74) *Attorney, Agent, or Firm* — Thompson Hine LLP

(57) ABSTRACT

A method to provide a therapeutic agent to an eye of a patient by implanting or inject a device that stably fits a particular location or position in the eye. The method thus provides agent inside the eye for a longer duration of agent release over a space-occupying area inside the eye.

21 Claims, 3 Drawing Sheets

(56) References Cited

OTHER PUBLICATIONS

Ding, J., et al. Fasudil protects hippocampal neurons against hypoxia-reoxygenation injury by suppressing microglial inflammatory responses in mice. *J Neurochem.* Sep. 2010;114(6):1619-29.

Boé, D., et al. Acute and chronic alcohol exposure impair the phagocytosis of apoptotic cells and enhance the pulmonary inflammatory response. *Alcohol Clin Exp Res.* Oct. 2010;34(10):1723-32.

Yu, J., et al. Therapeutic potential of experimental autoimmune encephalomyelitis by Fasudil, a Rho kinase inhibitor. *J Neurosci Res.* Jun. 2010;88(8):1664-72.

Yin, H., et al. 2-methoxyestradiol inhibits atorvastatin-induced rounding of human vascular smooth muscle cells. *J Cell Physiol.* Mar. 2010;222(3):556-64.

Chiba, Y., et al. Synergistic effects of bone marrow stromal cells and a Rho-kinase (ROCK) inhibitor, Fasudil on axon regeneration in rat spinal cord injury. *Neuropathology.* Jun. 2010;30(3):241-50.

Zimering, M., et al. Autoantibodies in type 2 diabetes induce stress fiber formation and apoptosis in endothelial cells. *J. Clin Endocrin Metab.* Jun. 2009;94(6):2171-7.

Krawetz, R., et al. Human embryonic stem cells: caught between a ROCK inhibitor and a hard place. *Bioessays.* Mar. 2009;31(3):336-43.

Claassen, D., et al. ROCK inhibition enhances the recovery and growth of cryopreserved human embryonic stem cells and human induced pluripotent stem cells. *Mol Reprod Dev.* Aug. 2009;76(*):722-32.

Wataya, T., et al. Human pluripotent stem cell and neural differentiation. (Written in Japanese.) *Brain Nerve.* Oct. 2008; 60(10):1165-72.

Akhmetshina, A., et al. Rho-associated kinases are crucial for myofibroblast differentiation and production of extracellular matrix in scleroderma fibroblasts. American College of Rheumatology, vol. 58, No. 8, Aug. 2008, pp. 2553-2564.

Tanihara, H., et al. Intraocular pressure-lowering effects and safety of topical administration of a selective ROCK inhibitor, SNJ-1656, in healthy volunteers, Arch Ophthalmol, Mar. 2008; 126(3), pp. 309-315.

Routhier, A., et al. Pharmacological inhibition of Rho-kinase signaling with Y-27632 blocks melanoma tumor growth. *Oncol Rep.* 23:861-867, 2010.

Thomas, S., et al. Src andCaveolin-1 reciprocally regulate metastasis via a common downstream signaling pathway in bladder cancer. *Cancer Res.* Dec. 10, 2010. [Epub. ahead of print.].

Liu, Y., et al. Serotonin induces Rho/ROCK-dependent activation of Smads 1/5/8 in pulmonary artery smooth muscle cells. *Faseb J.* Jul. 2009;23(7):2299-306.

Street, C., et al. Pharmacological inhibition of Rho-kinase (ROCK) signaling enhances cisplatin resistance in neuroblastoma cells. *Int J Oncol.* Nov. 2010;37(5):1297-305.

Peyman, Intravitreal Injection of Therapeutic Agents, The Journal of Retinal and Vitreous Diseases (2009) vol. 29 No. 7.

\* cited by examiner

OPHTHALMIC DRUG DELIVERY SYSTEM AND METHOD

This application is a divisional of co-pending U.S. application Ser. No. 12/985,758 filed Jan. 6, 2011; which is a Continuation-in-Part of U.S. application Ser. No. 12/611,682 filed Nov. 3, 2009, which claims priority from U.S. Application No. 61/114,143 filed Nov. 13, 2008, each of which is expressly incorporated by reference herein in its entirety.

Figure 1:
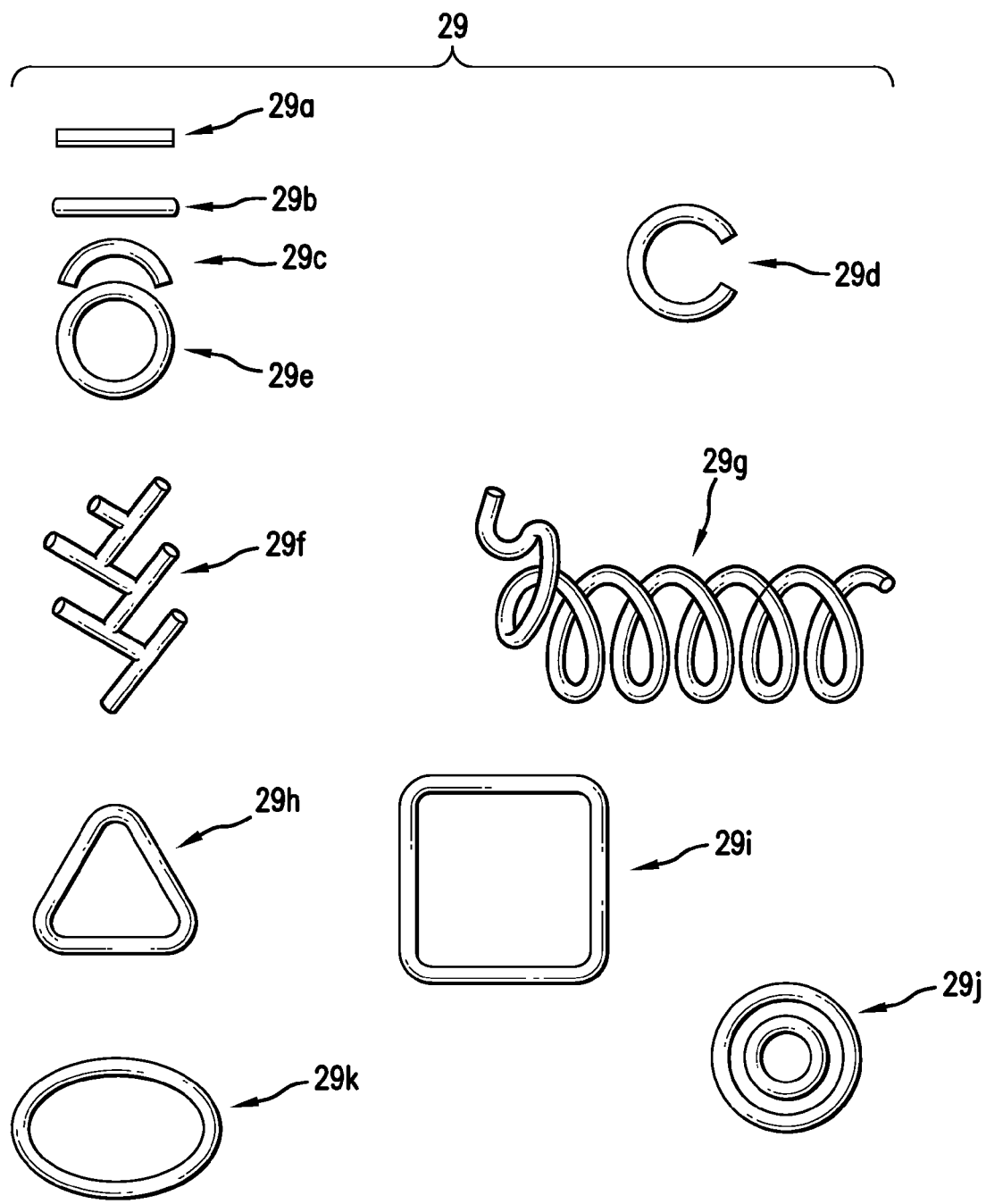
FIG. 1 shows embodiments of the device.
Figure 2A:
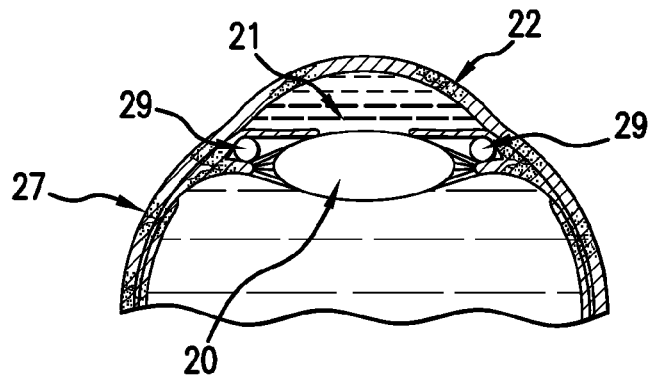
FIG. 2A shows a cross section of the lens capsule containing the pupil 21, cornea 22 and a device 29.
Figure 2B:
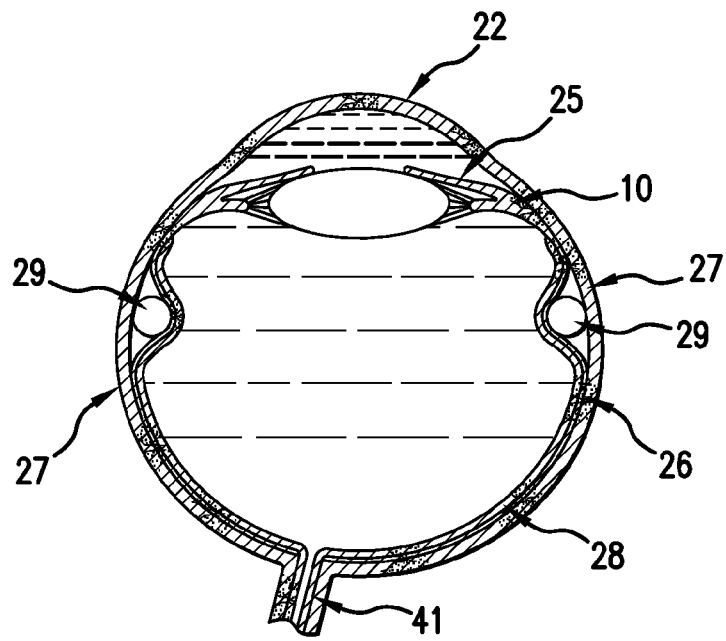
FIG. 2B shows a cross section of the eye depicting the supra choroidal space and the device 29 in relation to the cornea 22 and optic nerve 41.
Figure 2C:
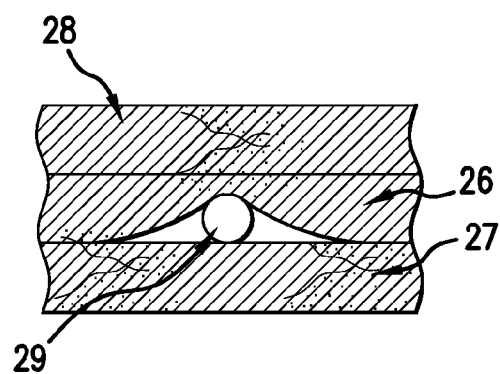
FIG. 2C shows a cross section of the eye wall.
Figure 2D:
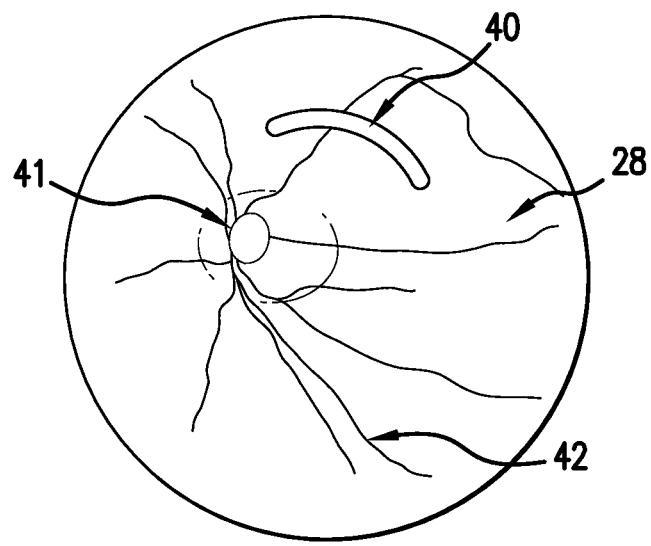
FIG. 2D shows a front view of the retina with optic nerve 41 and retinal vessels 42.
Figure 2E:
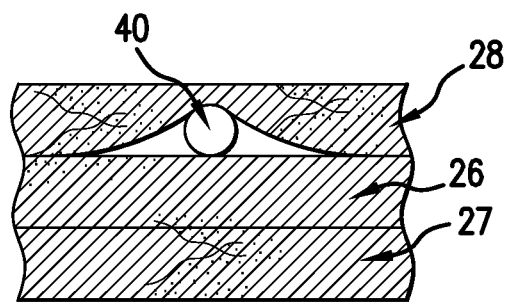
FIG. 2E shows the eye wall and subretinal implant 40.

Known methods of drug delivery to the eye have drawbacks, as the following illustrations demonstrate. Topical drug deliver must be repeated many times on a daily basis because of low or slow penetration. Compliance is also a problem. Subconjunctival drug delivery can be painful and has slow drug penetration. Intravitreal drug delivery has a short duration, typically of 2 to 30 days, so additional intervention and/or repeated injections are needed. The possibility of potential infections and retinal injury are also problems. Scleral implants and trans-scleral implants have not been attempted or tested. The implanted 29 devices usually are made of polymers; there is usually slow intraocular penetration when polymers are injected into the eye. The vitreous usually requires additional intervention with attendant potential complications, such as infection, retinal injury, etc.

Method of intraocular delivery of various therapeutic agents and methods are disclosed in Peyman et al., Retina, The Journal of Retinal and Vitreous Diseases 29 (2009) 875-912, which is expressly incorporated by reference in its entirety.

The disclosed system and method uses the capsular bag, obtained during or after cataract extraction, as a polymeric slow release drug delivery system and method. It is used for drug delivery and for simultaneous support for the lens capsule.

The inventive system is used during or after intra-ocular surgery for cataract extraction in the same session. After an opening in the anterior chamber is made, a circular area of the anterior capsule is removed to extract the lens cortex and nucleus.

In one embodiment, the system and method is used post-surgically to prevent or to treat inflammation. After surgery, most if not all eyes have some inflammation for which treatment is administered. For example, all patients who have diabetic retinopathy have post-surgical ocular inflammation. All patients who have a previous history of uveitis have more excessive inflammation.

In one embodiment, the device 29 is a capsular ring of any size configured in a shape for implanting outside the crystalline lens 15. Thus, the device is not dependent on removal of the crystalline lens 15. In this embodiment, the device 29 is intraocular but is extralens, it is external to the lens. It is supported in the eye by the lens zonules or ciliary body 10.

In one embodiment, the device 29 is a capsular ring of any size configured in a shape for implanting over the lens capsule having an intraocular lens 20. In this embodiment, where the eye contains an intraocular lens 20, the device is configured for implanting between the iris 25 and the outer part of the lens capsule.

It is important that the device 29 shape fits its position, that is, its location, inside the eye. The length of the device fits a large space inside the eye, and provides a longer duration of agent release over a wider area inside the eye than known devices.

In one embodiment, the device 29 is configured for implanting anterior to the lens 15. In this embodiment, the device is configured either C-shaped 29d or ring shaped 29e to lay on the zonules or the anterior lens capsule or the intraocular lens (IOL) 20. Any other device shape would not be stable in this position, that is, this location.

In one embodiment, the device 29 is configured for implanting in the choroid 26. In this embodiment, the device is configured either as a rod 29a or as a snake-shaped semicircle 29c. In these configurations, the device follows the inside curvature of the sclera 27 and can readily snake inside the suprachoroidal space. Any other device shape would be difficult to configure in the suprachoroidal space, and could penetrate the choroid 26 and the retina 28 resulting in serious complications. Any other device shape may not sufficiently large to cover a relatively large area.

In one embodiment, the device 29 is configured for implanting under the retina 28, that is, for subretinal implantation. In this embodiment, the device is configured either as a rod 29a or as a semicircle 29c, following the curvature of the retina and the subretinal space. Although a circular device may be implanted under the retina 29, implanting would be difficult. A circular device would not follow the retinal curvature and would bulge the retina.

In all embodiments the device is biodegradable, also termed bioabsorbable; no foreign body remains in the eye after the device is absorbed.

FIG. 1 shows various embodiments of the device 29. The device is rod shaped 29a, 29b and may be straight, curved 29c, C-shaped 29d, closed loop 29e. Its length ranges from 1 mm to 60 mm inclusive. In one embodiment, its length ranges from 15 mm to 600 mm inclusive. Its diameter ranges from 30 micrometers to 3 millimeters inclusive and is round, flat, bead-shaped, etc. The device is made of biodegradable polymers that contain and release agent contained within the device and/or within the polymers. In one embodiment the device is solid. In one embodiment the device is not-solid. In either embodiment, the device may be sized to be between 8 mm diameter and 18 mm diameter, inclusive.

The device 29 is shaped as a rod 29a, tube 29b, open loop 29c, 29d or closed loop 29e. In embodiments where the device is a rod 29a, the device can be a solid rod or a hollow tube with closed ends. The device is folded for easy implanting through an incision that is as small as 1 mm. The nanlded over the lens capsule in the posterior chamber. For implanting, a viscoelastic substance is also implanted for lubrication and ease of implantation, as known to one skilled in the art. Once the device is it in place, the device is unfolded.

For a suprachoroidal implantation application, the device 29 is shaped as a rod 29a, tube 29b or open loop 29c, 29d. It is not shaped as a closed loop. The device is implanted under the sclera 27 over the ciliary body 10 or the choroid 26 of the eye through a small incision, preferably in the sclera 27 at the plars plana area 1 mm to 4 mm behind the limbus of the cornea/sclera junction, or anywhere else in the sclera 27. The incision reaches the ciliary body 10/choroid 26. The space between the ciliary body 10/choroid 26 and the sclera 27 is called suprachoroidal space. The device which has a semicircular 29c, 29d or straight rod 29a configuration is threaded in the suprachoroidal space in any desired direction toward any meridian. The resilient structure of the device assists in moving it in this space to the desired length. Because of its round tip, it cannot penetrate the choroidal vessels but follows the suprachoroidal space when pushed against the resilient sclera. Its location can also be verified by indirect ophthalmoscopy. After the implantation, the scleral incision is closed with a suture.

For a subretinal implantation application, the device 29 is shaped as a rod 29a, tube 29b, or semicircle 29c. The device is implanted through a pars plana vitrectomy through the sclera 27. A subretinal bleb is created using a balanced saline solution at the desired retinal location, e.g., in the superior retina. Using forceps, the device 29 is inserted gently into the subretinal space where it remains until it is adsorbed. It is known that material injected under the retina 28, with time, diffuses from that location into the subretinal space under the macula and exerts a therapeutic effect.

Implantation methods are known to one skilled in the art. Implantation may use forceps. Implantation may use an injector.

In one embodiment, the device 29 contains agents that are neuronal cell protective and/or neuronal cell proliferative. The agents can be on the device, in the device, both on and in the device, and/or administered with the device by, e.g., simultaneous or substantially simultaneous injection upon implantation. Such devices are used for implanting in patients with glaucoma, neurodegenerative diseases including dry or wet forms of age related macular degeneration (ARMD), retinitis pigmentosa where the retinal cells and retinal pigment epithelial cells die by aging and genetic/inflammatory predisposition, and diabetic retinopathy.

One non-limiting example of such an agent is rho kinase (ROCK). ROCK plays an important role in cell proliferation, cell differentiation and cell survival/death. Blockade of ROCK promotes axonal regeneration and neuron survival in vivo and in vitro, thereby exhibiting potential clinical applications in spinal cord damage and stroke. ROCK inhibitors attenuated increases in pulmonary arterial pressures in response to intravenous injections of serotonin, angiotensin II, and Bay K 8644. Y-27632, sodium nitrite, and BAY 41-8543, a guanylate cyclase stimulator, decreased pulmonary and systemic arterial pressures and vascular resistances in monocrotaline-treated rats.

Its use to prevent and/or treat in degenerative retinal diseases such as ARMD, retinitis pigmentosa, and glaucoma has not been reported and thus is new. ARMD can have an inflammatory component, contributing to cell death and apoptosis. Oxidative and ischemic injury in ARMD and diabetic retinopathy also contributes to ROCK activation. Because ROCK plays an important role in these processes, inhibiting ROCK can prevent neuronal cell death.

In one embodiment, ROCK inhibitors are injected directly into the eye, e.g., in the vitreous cavity, under the retina 28, under the choroid 26, etc. Methods and formulations are disclosed in the following references, each of which is expressly incorporated by reference in its entirety: Peyman et al. Retina 7 (1987) 227; Khoobehi et al., Ophthalmic Surg. 22 (1991) 175; Berger et al., Investigative Ophthalmology & Visual Science, 37 (1996) 2318; Berger et al., Investigative Ophthalmology & Visual Science, 35 (1994) 1923. In one embodiment, ROCK inhibitors are injected in a polymeric formulation to provide a slow release system. In this embodiment, the polymeric material is made from any biodegradable polymer as known to one skilled in the art. Examples of suitable materials include, but are not limited to, polymers and/or co-polymers (poly)lactic acid (PLA), (poly)glycolic acid (PGA), lactic acid, (poly)caprolactone, collagen, etc. These can be injected or implanted in a shape and location as described above. In one embodiment, ROCK inhibitors are administered in a slow release system.

In one embodiment, ROCK inhibitors are administered with one or more other agents that inhibit inflammatory processes, inhibit angiogenesis, and/or inhibit fibrosis. Such agents include, but are not limited to, vascular endothelial growth factor (VEGF) inhibitors, platelet-derived growth factor (PDGF) inhibitors, and integrin inhibitors. In one embodiment, ROCK inhibitors are administered in a non-slow release form, and VEGF, PDGF, and/or integrin inhibitors are administered in a slow release form. In one embodiment ROCK inhibitors are administered in a slow release form, and VEGF, PDGF, and/or integrin inhibitors are administered in a non-slow release form. In one embodiment, ROCK inhibitors and VEGF, PDGF, and/or integrin inhibitors are administered in a dual, triple, or quadruple slow release form.

Examples of ROCK inhibitors include, but are not limited to, the following agents: fasudil hydrochloride (inhibitor of cyclic nucleotide dependent- and rho kinases); GSK 429286 (a selective ROCK inhibitors); H 1152 dihydrochloride (a selective ROCK inhibitor); glycyl-H 1152 dihydrochloride (a more selective analog of H 1152 dihydrochloride); HA 1100 hydrochloride (a cell-permeable, selective ROCK inhibitor); SR 3677 hydrochloride (a potent, selective ROCK inhibitor); Y 39983 dihydrochloride (a selective ROCK inhibitor); and Y 27632 dihydrochloride a selective p160 ROCK inhibitor). VEGF inhibitors include, but are not limited to, Avastin, Lucentes, etc. PDGF inhibitors include, but are not limited to, Sunitinib. Integrin inhibitors are known to one skilled in the art.

The concentration of ROCK inhibitor is administered so that its concentration upon release ranges from less than 1 micromol to 1 millimole. In one embodiment, the concentration of agent is administered so that its concentration upon release ranges from 1 micromole/day to 100 micromol day. Such concentrations are effective and are non-toxic.

The agents may be in any biocompatible formation as known to one skilled in the art. The agents may be formulated as microspheres, microcapsules, liposomes, nanospheres, nanoparticles, etc. as known to one skilled in the art.

The general configuration of the device 29 is new. The device is implanted by any of three different methods in various parts of the eye. In one method, the device is configured for implanting over the lens capsule and between the iris 25 and the lens 15 in the posterior chamber. In one method, the device 29 is configured for implanting in the suprachoroidal space; in this embodiment, agent contained in and/or on or with the device is delivered to the choroid 26 and retina 28. In one method, the device 29 is configured for implanting in the subretinal space; in this embodiment, agent contained in and/or on or with the device is delivered to the sensory retina.

In an intralens device, the device 29 may be of any shape. The following embodiments are illustrative only and are not limiting. In one embodiment, the device is ring shaped 29e, 29f. In one embodiment, the device is shaped as an open ring 29e (e.g., doughnut or tire shape). In one embodiment, the device is shaped as a rod 29a, 29b, which may be straight or curved 29c, 29d. In one embodiment, the device 29 is shaped as a semicircle 29c. In one embodiment, the device 29 contains one ring 29e. In one embodiment, the device contains at least two concentric rings 29j. In one embodiment, the device 29 is shaped as an oval 29k. In one embodiment, the device 29 is C shaped 29d. In one embodiment, the device 29 is shaped as triangle 29h. In one embodiment, the device 29 is shaped as a quadratic 29i. In one embodiment, the device 29 is spring-shaped 29g. In one embodiment, the device 29 is shaped in a zigzag configuration 29f. A tube structure permits delivery of agent that must be in a liquid medium, such agents include agents for gene modification or stem cells.

In one embodiment, the size of the device 29 ranges from 1 mm in diameter up to about 34 mm in diameter. In one embodiment, the size of the device 29 ranges from 1 mm in diameter up to about 20 mm in diameter. In one embodiment, the thickness of the device 29 may range from about 50 μm to about 3000 μm. In one embodiment, the thickness of the device 29 may range from about 10 μm to about 3000 μm. In one embodiment, the device 29 is made from a polymeric material that is absorbable. In one embodiment, the device 29 is made from a polymeric material that is nonabsorbable, e.g., polylactic acid polyglycolic acid, silicone, acrylic, polycaprolactone, etc. In one embodiment, the device 29 is made as microspheres.

The device 29 is positioned in the lens capsule, e.g., after cataract extraction prior to or after IOL implantation. In one embodiment, it is positioned inside the lens capsule after cataract extraction and acts as a polymeric capsular expander keeping the capsular bag open for intraocular lens (IOL) implantation). In one embodiment, the device 29 is positioned on the haptics of the IOL. In one embodiment, the device 29 is located inside the capsule or under the iris supported by the lens zonules, or it can be sufficiently large to lie in the ciliary sulcus, or ciliary body, or hanging from the zonules in a C-shaped configuration.

For implantation, after removing the lens cortex and nucleus inside the capsule through a capsulotomy, the inventive device 29 is implanted before or after an IOL is implanted. The inventive device 29 is flexible, deformable, and re-moldable. In one embodiment, the inventive device 29 is implanted through a incision one mm or less using an injector, forceps, etc. The incision may be made in the cornea for cataract removal. In one embodiment, the inventive device 29 is implanted in an eye without cataract extraction. In this embodiment the inventive device 29 may be implanted under the iris, e.g., after traumatic anterior segment injury, and lies over the crystalline lens, IOL, and zonules. Implantation may be facilitated by using a viscoelastic material such as healon, methyl cellulose, etc.

Retino-choroidal diseases are aggravated after cataract surgery. Retino-choroidal diseases include, but are not limited to, diabetes, existing prior inflammations such as uveitis, vascular occlusion, wet age related macular degeneration, etc. Patients with these diseases are candidates for the inventive drug delivery system and method. Other indications are prophylactic therapy prior to development of retinal complications, such as inflammation (CME) and infection, and therapy for an existing disease. Other indications are conditions in which any intraocular drug delivery to treat aging processes if cataract surgery is contemplated or after IOL implantation. In latter situation, the inventive device can be implanted in the capsule or over the IOL under the iris Other indications are post-surgical inflammations, post-surgical infections such as after cataract extraction, and any intraocular delivery.

In one embodiment, medication can be coated on a surface and eluted from the surface of the inventive device for delivery, using methods known in the art (e.g., drug-coated stents). In one embodiment, medication can be incorporated in the polymeric material using methods known to one skilled in the art. The following medications can be delivered, alone or in combinations, to treat eyes using the inventive system and method: steroids, non-steroidal anti-inflammatory drugs (NSAIDS), antibiotics, anti-fungals, antioxidants, macrolides including but not limited to cyclosporine, tacrolimis, rapamycin, mycophenolic acid and their analogs, etc. For example, voclosporin (FIG.) is a next generation calcineurin inhibitor, an immunosuppressive compound, developed for the treatment of uveitis, an inflammation of the uvea, the treatment of psoriasis, and for the prevention of organ rejection in renal transplant patients. It can be used with other immunomodulatores, etanercept, infliximab, adalimumab, etc. Other examples include: antibodies (e.g., anti-vascular endothelial growth factor), immunomodulators, antiproliferative agents, gene delivery agents (e.g., to treat damaged neuronal tissue), neuroprotective agents, anti-glaucoma agents (e.g., to treat or prevent increases in intraocular pressure, etc.). In one embodiment, combinations of agents may be provided in a single device or in multiple devices.

The duration of delivery is manipulated so that the agent(s) is released at a quantity needed to achieve therapeutic effect for each agent, if more than one agent is administered, as long as necessary. Duration may be a single dose, may be one day, may be daily for up to 12 months or longer, may be several times a day. In embodiments using a polymer, reimplantation is possible through a small incision once the polymer is absorbed.

Other variations or embodiments will be apparent to a person of ordinary skill in the art from the above description. Thus, the foregoing embodiments are not to be construed as limiting the scope of the claimed invention.

What is claimed is:

1. A method of providing a therapeutic agent to an eye of a patient, the method comprising
providing to an eye of the patient a device that is 15 mm to 60 mm in length, deformable, biodegradable and absorbable and containing at least one of:
(i) a therapeutic agent selected from the group consisting of a rho kinase inhibitor, a platelet-derived growth factor inhibitor, and an integrin inhibitor; and
(ii) stem cells released upon injecting in the patient's eye, a releasable neuronal cell protective agent and optionally other agents, the device shaped to stably fit a suprachoroidal or subretinal position in the eye choroid or on the lens zonules, and sized to occupy the choroidal space inside the eye or the space on the lens zonules to provide a relatively longer duration of agent release over a relatively larger space-occupying area inside the eye; and
implanting the device suprachoroidially between the sclera and the choroid posteriorly with respect to the pars plana of the eye or subretinally following the curvature of the retina and subretinal space but not bulging the retina.

2. The method of claim 1 further comprising implanting the device suprachoroidially in the suprachoroidal space and the agent is contained in and/or on or with the device delivered to the choroid and retina.

3. The method of claim 1 further comprising implanting the device subretinally in the subretinal space and the agent is contained in and/or on or with the device delivered to the sensory retina.

4. The method of claim 1 where the patient has an ocular disease.

5. The method of claim 1 performed during ocular surgery.

6. The method of claim 1 performed after ocular surgery to prevent ocular inflammation.

7. The method of claim 1 where the neuronal cell protective therapeutic agent is a rho kinase inhibitor.

8. The method of claim 1 where the device is provided by an incision as small as 1 mm.

9. The method of claim 1 providing the device with forceps.

10. The method of claim 1 where the device is provided by injecting the device.

11. The method of claim 1 where the device is provided by folding the device for providing the device to the eye, then unfolding the device once the device is in the eye.

12. The method of claim 1 where the device further includes additional other therapeutic agents selected from the group consisting of a vascular endothelial growth factor inhibitor, a platelet derived growth factor inhibitor, an integrin inhibitor, and combinations thereof.

13. The method of claim 1 where the patient has a retinal degenerative disease.

14. The method of claim 1 where the device has one of the following shapes: (i) a rod shape, (ii) a tube shape, (iii) snake-shaped semicircle, or an (iv) open loop shape, but not a closed loop shape.

15. The method of claim 1 where the device has semicircle shape, but not a circular shape.

16. A method of providing a therapeutic agent to an eye of a patient, the method comprising providing to an eye of the patient a device that is 15 mm to 60 mm in length, deformable, biodegradable and absorbable and containing at least one of: (i) a therapeutic agent selected from the group consisting of a rho kinase inhibitor, a platelet-derived growth factor inhibitor, and an integrin inhibitor; and (ii) stem cells released upon injecting in the patient's eye, the device shaped to stably fit a position on the lens zonules, and sized to occupy a space inside the eye to provide a longer duration of agent release over a space-occupying area inside the eye; and implanting the device over the lens capsule and between the iris and the lens in the posterior chamber.

17. The method of claim 16 where the device is C-shaped or ring shaped.

18. The method of claim 16 where the therapeutic agent is a rho kinase inhibitor.

19. The method of claim 16 where the device is provided by an incision as small as 1 mm.

20. The method of claim 16 where the device is provided by folding the device for providing the device to the eye, then unfolding the device once the device is in the eye.

21. The method of claim 1 further comprising implanting the device containing agents that are neuronal cell protective and/or neuronal cell proliferative for therapy to the patient having or having a genetic predisposition to a neurodegenerative disease selected from the group consisting of a dry form of age related macular degeneration (ARMD), a wet form of ARMD, retinitis pigmentosa, diabetic retinopathy, and combinations thereof.

* * * * *